United States Patent [19]

Saadatmanesh et al.

[11] Patent Number: 5,242,438
[45] Date of Patent: Sep. 7, 1993

[54] METHOD AND APPARATUS FOR TREATING A BODY SITE WITH LATERALLY DIRECTED LASER RADIATION

[75] Inventors: Vahid Saadatmanesh, Irvine; Hany M. G. Hussein, Costa Mesa; Marvin P. Loeb; Stanislaw Sulek, both of Huntington Beach; James A. Milburn, Santa Ana, all of Calif.

[73] Assignee: Trimedyne, Inc., Irvine, Calif.

[21] Appl. No.: 689,456

[22] Filed: Apr. 22, 1991

[51] Int. Cl.⁵ ............................................. A61B 17/36
[52] U.S. Cl. ................................. 606/15; 606/7; 606/17
[58] Field of Search ............... 606/17, 18, 13, 14, 606/15, 16, 7, 6

[56] References Cited

U.S. PATENT DOCUMENTS

| | | | |
|---|---|---|---|
| 4,207,874 | 6/1980 | Choy | 606/7 X |
| 4,768,858 | 9/1988 | Hussein | 350/96.32 |
| 4,784,132 | 11/1988 | Fox et al. | 606/15 |
| 4,819,632 | 4/1989 | Davies | 606/16 X |
| 4,820,015 | 4/1989 | Mogi | 350/96.24 |
| 4,832,024 | 5/1989 | Boussignac et al. | 606/15 X |
| 4,852,567 | 8/1989 | Sinofsky | 606/7 X |
| 5,041,121 | 8/1991 | Wondrazek | 606/15 |

*Primary Examiner*—Peter A. Aschenbrenner
*Attorney, Agent, or Firm*—Dressler, Goldsmith, Shore, Sutker & Milnamow, Ltd.

[57] ABSTRACT

A method and device are provided for directing laser radiation to a body cavity site. A hollow, elongate, optical fiber is advanced, usually in a containing device, to the vicinity of the site and coupled to a laser source with a distal end region of the fiber extending along a longitudinal axis. The fiber terminates in an energy delivery surface for emitting laser radiation transmitted by the fiber. The radiation is intercepted at a location axially aligned with the energy delivery surface and is reflected in a beam radiating substantially transversely of, and substantially circumferentially around, the axis. A reflector member or block is provided for reflecting the radiation and is mounted in an open end of the catheter at a selected axial position along the axis. A fluid, such as a flushing fluid, can be directed between the end of the fiber, against the reflector member, and to the body site.

9 Claims, 4 Drawing Sheets

METHOD AND APPARATUS FOR TREATING A BODY SITE WITH LATERALLY DIRECTED LASER RADIATION

TECHNICAL FIELD

The present invention relates to medical devices and procedures for treating a site in a patient's body with laser energy transmitted through an optical fiber.

BACKGROUND OF THE INVENTION AND TECHNICAL PROBLEMS POSED BY THE PRIOR ART

Various instruments have been developed or proposed for applying laser radiation through a flexible, optic fiber to internal body sites. The fiber can be positioned in a body cavity or passage. Typically, the fiber is advanced through an endoscope or other surgical tool into a body cavity, artery, or other body passage to a selected internal treatment location.

Instruments of the above-described type may be broadly defined as laser catheters. As used in this specification and in the claims, the term "laser catheter" or "catheter" is intended to broadly include a flexible, or even rigid, instrument for being inserted into a natural or surgically created internal passage or cavity in a body and through which laser energy is transmitted.

A number of designs have been proposed for a laser catheter which can be inserted into a body passage and operated to direct the laser radiation laterally to the surrounding site in the body cavity. U.S. Pat. Nos. 4,445,892 and 4,785,815 and published PCT application PCT/US89/02492 disclose designs for a laser catheter wherein the radiation is reflected laterally by a mirror. The optic system disclosed in the U.S. Pat. No. 4,445,892 can be rotated with respect to the longitudinal axis so as to sweep through a 360 arc. The mirror can also be pivoted on a ball-and-socket joint by means of guide wires.

While these designs may be effective in applications for which they are intended, it would be desirable to provide an improved laser catheter device which could be efficiently employed in a variety of medical procedures. For example, in prostatic resection or endometrial (uterine) ablation, an electrocautery device or laser catheter device is dragged or otherwise moved slowly back and forth generally in rows along the tissue, and this is a tedious, 45-60 minute procedure which can produce uneven results. Thus, it would be beneficial if an improved device could provide radiation in a 360 beam via a relatively simple transmission system that does not require excessive movement or rotation of the catheter or catheter components.

Some patents disclose devices for directing laser radiation laterally and around a longitudinal axis without rotation of internal components. For example, U.S. Pat. No. 4,672,961 discloses a device in which a special, parabolic reflecting surface is employed in conjunction with a plurality of circumferentially spaced optical fibers mounted in a template around a guiding tube, and this assembly is carried within a surrounding tube that slides within a fixed outer tube.

U.S. Pat. No. 4,852,567 discloses a laser tipped catheter in which laser radiation is radially directed by employing a defusing tip on a tapered optical fiber or by employing a conical reflecting surface disposed in the beam path of a plurality of circumferentially spaced optical fibers.

U.S. Pat. No. 4,799,479 discloses a type of laser catheter in which the cladding is removed from an area along the optical fiber and in which the optical fiber core is abraded so that the fiber surface is roughened. This effects a lateral diffusion of the laser radiation.

While the above-discussed designs can function to radiate laser energy generally transversely of, and around, the longitudinal fiber axis, it would be desirable to provide an improved device which can accurately control the radiation beam and yet does not require special modifications to an optical fiber or require complex arrangements of multiple optical fibers.

It would also be advantageous if such an improved device could efficiently transmit the radiation laterally with a minimum of dispersion, attenuation, or other radiation beam losses.

Finally, although the use of flushing liquids with catheters is known (e.g., U.S. Pat. Nos. 4,445,892 and 4,773,413) it would also be desirable if an improved device and treatment method could be provided to effect the flushing of the body site with fluid while at the same time directing the laser radiation laterally to the body site.

The present invention provides an improved laser radiation delivery method and catheter suitable for coupling to a laser source to direct radiant laser energy laterally to a selected body cavity site, and the invention can accommodate designs having the above-discussed benefits and features.

SUMMARY OF THE INVENTION

The present invention is embodied in a medical device or catheter for laterally applying radiant energy to a selected body site, and is embodied in a method of so applying such energy. In accordance with the apparatus and method aspects of the invention, at least some of the laser energy transmitted along an optical fiber is dispensed adjacent the distal end of the fiber as a laser beam radiating substantially perpendicularly to, and around, the longitudinal axis of the optical fiber at the distal end thereof. In this manner laser energy may be applied to the body site in a controlled beam for performing a medical procedure.

The catheter of the present invention permits placement of the catheter under direct vision, or by means of fluoroscopy or ultrasound. The device is especially suitable for use in prostatic resection or endometrial (uterine) ablation. Once the device is in place, it is easily operated (e.g., for about 4 minutes at 60 watts power when used for prostatic resection).

The apparatus aspect of this invention contemplates an elongated, laser energy transmitting conduit that is provided with reflector means at its distal end, and that can be optically coupled at its proximal end to a laser energy source. In some preferred embodiments, the reflector means is substantially conical.

The reflector means is mounted at, but spaced from, the distal end of the laser-transmitting conduit so that a laser beam impinging thereupon is reflected radially outwardly toward a selected body site that is to be irradiated. The apex of the reflector means is pointed toward the terminus of the optical fiber. The axis of symmetry of the reflector means is substantially aligned with the longitudinal axis of the optical fiber at its distal end. In this manner, the laser energy transmitted by the fiber is reflected outwardly around the reflector means without a substantial amount of the laser energy being absorbed by the reflector means and converted into heat.

The reflector means can be held in a cage that receives the distal end of the optic fiber so that the reflector means is held in a maintained position relative to, but spaced from, the optical fiber. In the preferred embodiments of the invention, an internal region of the catheter is open adjacent the reflector means. Thus, the laterally directed radiation is not substantially attenuated by intervening components. Further, means are provided for introducing a fluid through or to the catheter opening adjacent the reflector means. This can be used for cooling the reflector means or for flushing or treating the body site.

A method aspect of this invention contemplates the introduction of the present apparatus or device into, for example, a body cavity or lumen of a patient and thereafter irradiating a selected body site with a 360 circumferential laser beam of a desired intensity. In this manner coagulation, ablation, or vaporization can be effectively performed at the body site.

The laser radiation may be suitably produced by a conventional laser and may include infrared radiation (IR) and ultraviolet radiation (UV), as well as visible laser light. Examples of laser types that can produce suitable energies include: carbon dioxide, argon, holmium: yttrium aluminum garnet (holmium: YAG), neodymium: yttrium aluminum garnet (Nd:YAG), and excimer. The device is very effective in providing radiant energy for a range of laser radiation frequencies and types, particularly when the reflector means of the device is provided with a reflective surface of a suitable dielectric material or a metal coating of gold, copper, silver, platinum, or the like.

The novel radiation transmitting method and catheter device of the present invention may be efficiently employed with a single, optic fiber. Further, the flushing fluid can be relatively simply and effectively directed to the site with designs embodying the present invention. The fluid may be provided through special internal passages in the catheter or around the catheter through an endoscope or other surgical tool into which the catheter is inserted.

The present invention can also be embodied in designs which employ a thermocouple or other thermal sensing means for detecting excessive heating of the reflector means which could occur in some circumstances (e.g., tissue adherence to the reflector means or excessively long periods of laser operation). The thermocouple can be provided as part of a control system for reducing or terminating the emission of the laser radiation in such circumstances.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

The apparatus of the present invention is embodied in a medical device for applying radiant laser energy laterally to a selected body site in an efficient manner that minimizes trauma to the site.

The device of the present invention can be operated to irradiate the body site with a 360° circumferential laser energy beam of a desired intensity without requiring rotation of the device in the cavity. The radiation beam is directed to the site without passing through intervening covers or windows that can attenuate, refract, disperse, or otherwise interfere with the beam. This beam can be used in a variety of medical procedures for effecting coagulation, ablation, vaporization, and the like.

The device incorporates a single optic fiber to thereby reduce the complexity found in some prior art designs. The device also can provide flushing fluid to the site.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

The apparatus of this invention may be employed with a suitable conventional laser and coupling system therefor, the details of which, although not fully illustrated or described, will be apparent to those having skill in the art and an understanding of the necessary functions of such devices. The detailed descriptions of such devices are not necessary to an understanding of the invention and are not herein presented because such devices form no part of the present invention.

Figures 1, 2, 3:
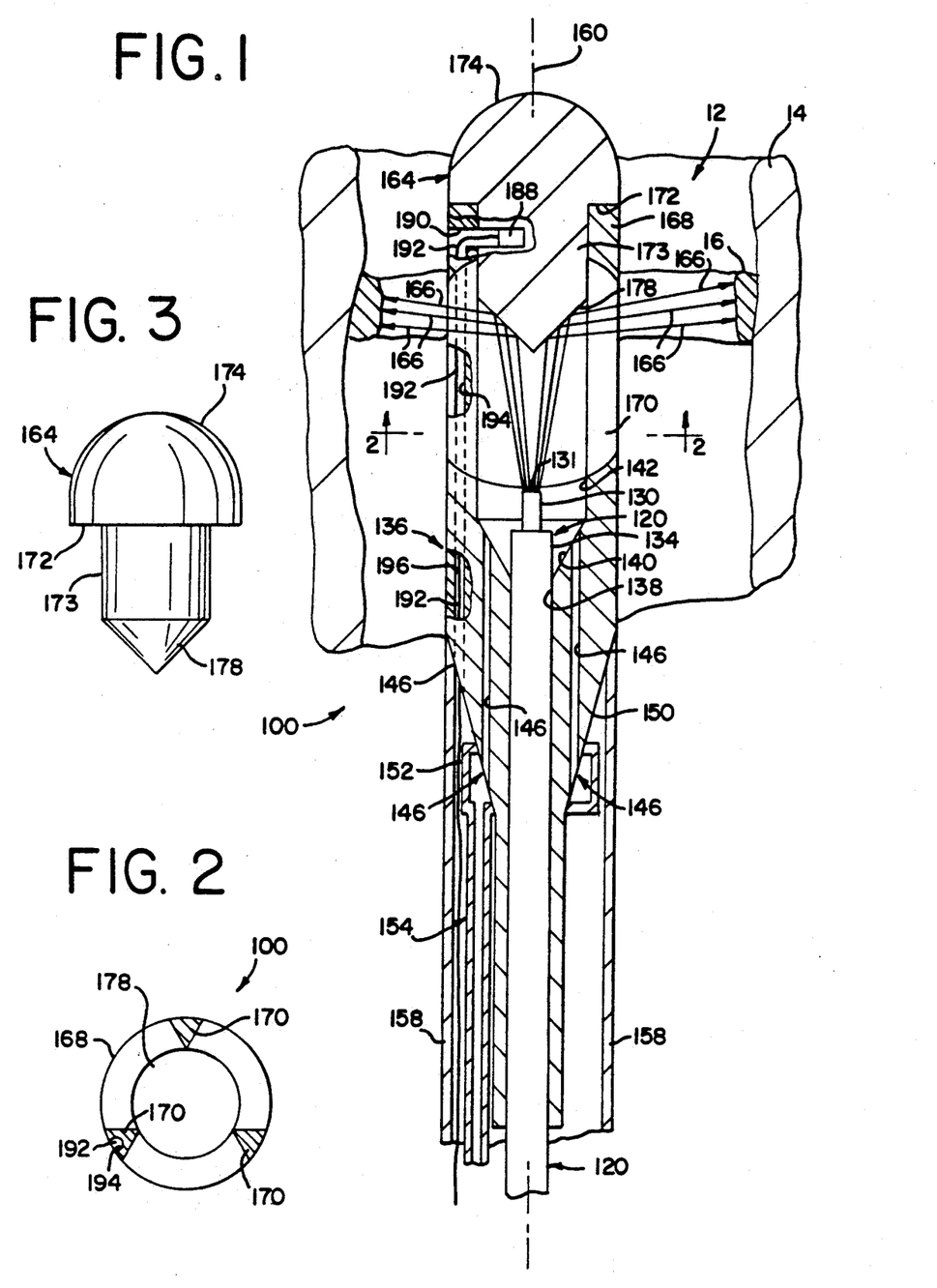
FIG. 1 is a fragmentary, side elevational view, partly in cross section, showing the distal end portion of a catheter embodying the present invention and received within a body cavity.
FIG. 2 is a cross-sectional view taken generally along the plane 2—2 in FIG. 1.
FIG. 3 is a side elevational view of the reflector end member prior to assembly in the catheter illustrated in FIG. 1.

Referring now to FIG. 1, a medical device in the form of a catheter 100 embodying the present invention is shown positioned within a body passage or cavity 12. The catheter may be inserted, if desired, through an endoscope, cannula, or other surgical tool (not illustrated). The cavity 12 may be a natural or surgically created cavity or passage in body tissue 14. For example, the tissue 14 may define a blood vessel or duct, or other cavity in an organ.

A portion of the cavity 12 may be characterized as defining a body site containing a material 16 which is to be altered by application of laser radiant energy. The material 16 may be a part of the tissue 14 per se or may be an altered form of the tissue 14, such as cancerous tissue. The material 16 could also be an additional deposit on the tissue 14. For example, such a deposit may be a clot, fat, or arteriosclerotic plaque.

The catheter 100 of the present invention is especially suitable for use in a body cavity in which the material 16 to be altered by the radiation extends generally circumferentially around the interior of the cavity in a substantially 360° circumferential configuration toward the surrounding material 16.

The catheter 100 includes an optical fiber 120 which functions as an elongated, laser energy transmitting conduit. The optical fiber 120 is adapted to be coupled at its proximal end to a laser energy source (not illustrated) which generates and supplies radiant laser energy to the fiber 120. The terms "laser energy", "laser radiation", "laser beam" and variants thereof as used in this specification disclosure and in the claims will be understood to encompass a broad range of radiation frequencies, characteristics, and energy densities. The laser radiation may be suitably produced by a conventional laser such as, for example, a laser of the neodymium:yttrium aluminum garnet (Nd:YAG) type. Other laser types may include carbon dioxide, argon, holmium:yttrium aluminum garnet (holmium:YAG), and excimer. Radiation that may be used in various applications can include infrared radiation (IR), ultraviolet radiation (UV), and visible light.

Conventional means (not illustrated) may be employed for injecting the radiant laser energy into the optical fiber 120 so that the energy will be transmitted along the fiber 120, and such means constitutes a coupling system between the focused radiant energy laser beam and the optic fiber 120. The design, construction, and operation of laser sources and coupling systems are well known in the art and are not described in detail herein. The details of the design, construction, and operation of such laser sources and coupling systems form no part of the present invention.

The fiber 120 is a single, solid elongate, unitary optical fiber having a core 130 which may be made of glass or silica quartz. The fiber core 130 terminates in a transverse, substantially flat, circular, energy delivery surface 131 and is covered with a thin cladding (not illustrated). The laser radiation transmitted along the fiber core 130 is emitted from the surface 131. Alternatively, in some applications, the fiber 120 may be formed from polymeric materials such as, for example, poly(methylmethacrylate) or polystyrene. The diameter of the core is preferably between about 300 microns (0.3 mm.) and about 1000 microns (1 mm.). In one contemplated embodiment of the present invention, the diameter of the core 130 is about 600 microns (0.6 mm.).

Various optical fibers that may be suitable for particular applications are commercially available. For example, a fiber optic having a core diameter of 0.4 mm. is marketed under the designation Med 400 by Quartz Products Corporation of Plainfield, N.J. A 0.6 mm. diameter fiber optic is commercially available under the designation HCT 600 from Ensign Bickford Co., Connecticut.

The power that can be transmitted along optical fiber varies with the size of the fiber. Utilizing the above-described HCT 600 fiber optic, a medical device embodying this invention can transmit as much as about 60 watts continuous power from a Nd:YAG laser source.

In a preferred embodiment, an outer sheath 134 is disposed to cover the thin cladding material (not illustrated) that surrounds the outer cylindrical surface of the core 130. The thin cladding material has a refractive index which differs from the refractive index of the fiber core 130. The material employed for the core outer cladding is selected on the basis of the refractive indexes relative to the core refractive index such that the laser radiation is confined within the fiber core 130 with a minimum attenuation. In some applications it may be desirable that the internal reflection caused by the cladding be such that the radiation emitted from the end of the fiber core 130 has a relatively low divergence.

Examples of suitable cladding materials include silicone, silica, air or plastic. Plastic material suitable for cladding includes poly(methylmethacrylate) or a mixture of poly(methylmethacrylate) and polystyrene. In a contemplated embodiment, the cladding is silicone.

The thickness of the sheath 134 that protects the cladding material is about 0.2 mm. The sheath material may be, for example, polyethylene.

Finally, in some applications it may be desirable to include an outer tubular covering (not illustrated), instead of, or in addition to, the sheath. The covering may be a synthetic resin polymer such as the polymer sold under the trademark TEFLON. Other materials that may be used for the cover include silicone rubber, natural rubber, polyvinyl chlorides, polyurethane, copolyester polymers, thermoplastic rubbers, silicone-polycarbonate copolymers, polyethylene ethyl-vinyl-acetate copolymers, woven polyester fibers, or combinations of these.

The wall of the catheter may be reinforced. Further, radiopacity can be obtained by incorporating lead or barium salts into the wall of the catheter.

The distal end of the fiber 120 is received in a tubular structure, housing, or head 136. The head 136 is preferably fabricated from surgical stainless steel and defines an internal bore 138 in which the fiber 120 is disposed. A distal end of the fiber 120 projects into an enlarged region in the head 136 that is defined by a frustoconical surface 140 and an enlarged bore 142. The head 136 defines an end region extending along a longitudinal axis 160 which is perpendicular to the energy delivery surface 131.

The catheter 100 may be positioned with the aid of fluoroscopy or ultrasound or by direct vision—depending upon the particular body site and procedure. In some treatment procedures, the catheter 100 is preferably advanced through an endoscope, cannula, or other surgical tool. If the catheter 100 is inserted through an endoscope, cannula, or other surgical tool, then fluid may be infused about the catheter body through the main passage in the tool or through a separate channel in the tool provided for that purpose. Such fluids can include flushing fluids or treatment fluids, such as saline, glycine, sterile water, gases (such as carbon dioxide), and oxygen bearing liquids. Drugs, such as an anti-coagulant, anti-spasmodic, anti-vasoconstrictive, or others, can be infused along with a flushing fluid. A radiopaque liquid can also be introduced for fluoroscopic viewing. In some cases, the fluid may be a heat transfer agent for use in heating or cooling the catheter components or body site. Also, suction could be effected around the catheter through the endoscope (or other tool).

The present invention also effectively accommodates a novel arrangement of passages for carrying such fluids within the catheter per se. In particular, the head 136 defines one or more channels or passages 146 for carrying fluid. Each passage 146 extends from the enlarged region at the frustoconical surface 140 to a rearwardly facing, angled, exterior surface 150. A generally annular, fluid distributing collar 152 is mounted to the surface 150 of the head 136 over the openings to the passages 146. A supply tube 154 is connected to the collar 152 for supplying a fluid to the head 136. In addition, suction could be drawn through the passage system 146, 152, and 154 to remove debris.

If desired, the rear portion of the head 136 can be covered with a suitable housing 158. The shroud 158 may extend beyond the rear end of the head 136 to a point on the catheter which is normally outside of the body cavity. Preferably, such a housing 158, as well as the tube 154 and fiber 120, are all flexible, at least rearwardly of the end of the head 136, so as to permit the catheter 100 to be advanced in a lumen or other body cavity.

In any event, the exterior surfaces of the catheter 100 which may come in contact with the body tissue should preferably be of materials which are biocompatible for the time period during which the catheter will be received within the body cavity.

A reflector means, such as a reflecting block in the form of a mirror or reflector member 164, is positioned axially adjacent the energy delivery surface 131 for intercepting and reflecting the emitted radiation in a beam that radiates substantially transversely of, and substantially around, the axis 160 as schematically indicated by the arrows 166.

The reflector member 164 is mounted on the end of the head 136 on a support ring 168 which is spaced from the fiber energy delivery surface 131. Preferably, the ring 168 is disposed at the end of two or more struts, such as three struts 170 which are unitary with the ring and with the portion of the head at the bore 142. As illustrated in FIG. 2, the struts 170 each have a generally triangular transverse cross section.

To aid in securely mounting the member 164 to the ring 168, the reflector member 164 defines a shoulder 172 and a reduced diameter cylindrical section 173. The member 164 can be retained within the ring 168 by suitable means, such as by welding, machine screws (not illustrated), adhesive, etc.

The reflector member 164 has a rounded front edge or end 174 which is smooth and which is adapted to gently slide past body tissue in the cavity 12 with a minimum of trauma to the tissue. The end of the reflector member 164 may include a separate member or piece of material (not illustrated) for providing a rounded surface, and such additional material may be a ceramic or other suitable material. Preferably, at least the rounded front surface 174 is coated with a non-stick or release coating such as polytetrafluoroethylene to provide easy release from tissue.

The reflector member 164 has a generally conical rear end that includes a conical reflecting surface 178 which is defined around a central axis that is coincident with the longitudinal axis 160. The conical surface 178 is oriented to diverge away from the axis 160 with increasing distance from the fiber energy delivery surface 131.

The conical reflecting surface 178 may be provided by a reflective layer of suitable material that is effective with the wavelength of the particular laser radiation. Examples of suitable materials include platinum, silver, copper, or gold. For example, a conventional gold plating that is commercially available is one marketed under the designation LASER GOLD by Epner Technology, Inc., 25 Division Place, Brooklyn, N.Y. 11222, U.S.A.

The reflecting coating is applied to a generally solid mass of material forming the reflector member 164. Preferably, the reflector member 164 is made of metal, such as surgical stainless steel, but could also be made of a combination of thermally conductive and thermally insulating materials such as metals and ceramics. The mass of metal forming the reflector member 164 functions as a heat sink for the small portion of the radiation energy which is absorbed and converted into heat at the reflecting surface 178.

In some applications, the reflector member 164 may be made from non-metallic materials, such as glass, diamond, or sapphire. Fused silica and glass sold under the trademark PYREX are preferred because of their high thermal shock resistance and relatively lower cost compared to diamond and sapphire. The reflective surface 178 may be provided on the glass in the form of a metallic film of dielectric. Metallic coatings can include aluminum, gold, silver, copper, platinum, and rhodium. A film of silicon monoxide or magnesium fluoride can be deposited over the metal for protection. A dielectric coating can be prepared by vacuum-deposition on the glass of alternate layers of magnesium fluoride and cerium dioxide films. The coating material and thickness depend on the angle of the reflecting surface 178 and on the wave length of the incident laser radiation.

Preferably, the angle of the conical reflecting surface, relative to the longitudinal axis 160, is about 45°. Most of the laser radiation (which is preferably emitted from the energy delivery surface 131 in a cylindrical beam or narrow cone beam along the axis 160) will then be reflected substantially transversely of, and substantially around, the axis 160. The reflected radiation 166 is thus laterally directed circumferentially to the target material 16 at the body cavity site.

Typically, according to the method of the present invention, the catheter 100 is advanced to the vicinity of the body cavity site with the reflector member 164 positioned at a selected axial location along the axis 160 so as to be able to irradiate the body site. As previously explained, in some treatment procedures the catheter is preferably advanced through an endoscope, cannula, or other surgical tool to the body site. Fluids, such as the above-discussed treatment fluids or flushing fluids, may be pumped through the endoscope, cannula, or other surgical tool or through the catheter channels 146 in the head 136 so that the fluid passes out of the head 136 between the struts 170 to the body site. The fluid may be directed over the reflector member 164—especially in those cases where the fluid is supplied through the head channels 146.

The laser radiation is transmitted through the fiber 120 and is emitted from the fiber end surface 131. The emitted radiation is intercepted by the reflector member 164, at a location which is exposed to the body cavity site, and the radiation reflected transversely of, and substantially around, the longitudinal axis 160 by the reflector member 164. Owing to the shape and small cross section of each of the struts 170 that support the mounting ring 168, the radiation is reflected in a substantially uninterrupted 360° beam. The struts 170 may be coated with a reflective material to further reduce the absorption of laser energy by the struts while reflecting the energy to the body site.

In some applications, it may be desired to provide a means for sensing the thermal energy of the reflector member 164. For example, in some applications, the temperature of the reflector member 164 should not be allowed increase too high above the ambient temperature. Material or materials used for fabrication of the reflector member 164 may dictate that the temperature increase be limited. Also, it may be desirable to limit the temperature of the reflector member 164 if the body site tissues are in contact with the reflector member 164 during the irradiation procedure. To this end, a thermocouple or other temperature sensing device may be provided in the catheter 100. In particular, FIG. 1 illustrates how a thermocouple junction 188 can be disposed within a bore 190 that is defined within the reflector member 164 and the adjacent support ring 168. The junction 188 may be fixed within the bore 190 by a suitable adhesive or epoxy (not illustrated).

The lead wires or cable 192 can be routed from the junction 188 through the bore 190 and along a channel 194 defined in the ring 168 and in an adjacent strut 170. A bore 196 is provided in the body 136 for running the thermocouple lead wires 192 from the strut channel 194 to the inside of the housing 158.

Preferably, the thermocouple 188 is provided as part of a control system (not illustrated) which operates an appropriate annunciator or alarm system when a predetermined set point temperature is reached. The control system may also operate to reduce the laser energy output or to completely terminate the operation of the laser. Such a temperature sensing control system is advantageously used where fluid flow is provided through the catheter to the reflector member 164 for purposes of cooling. In such cases, the temperature could increase if the laser is operated for too long a time period or if the cooling flow is obstructed (e.g., by tissue adherence to the reflector member 164). Such a temperature sensing and control system can effectively operate to prevent deterioration or destruction in those situations where excessive heat is absorbed by the reflector block 164.

Alternate embodiments of the device of the present invention are illustrated in FIGS. 4–12 wherein the elements are designated generally by three digit numbers. Elements of each of the alternate embodiments that are identical or functionally analogous to elements of the first embodiment illustrated in FIGS. 1–3 are designated by reference numbers in which the last two digits are identical to the last two digits of the reference number of the identical or functionally analogous element in the first embodiment.

Figure 4:
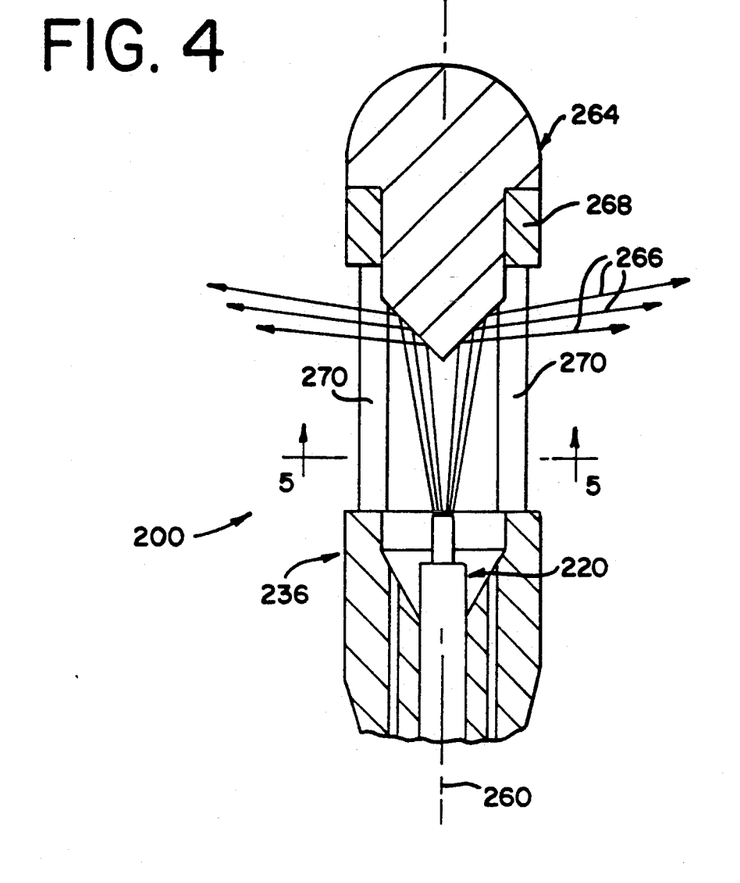
FIG. 4 is a fragmentary, side elevational view, partly in cross section, showing the distal end portion of a second form of a catheter embodying the present invention.
Figure 5:
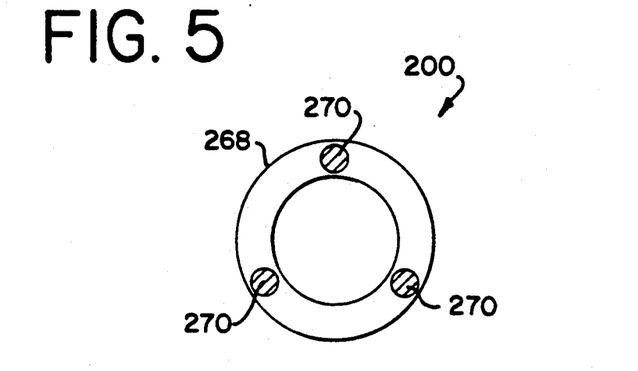
FIG. 5 is a cross-sectional view taken generally along the plane 5—5 in FIG. 4.
Figure 6:
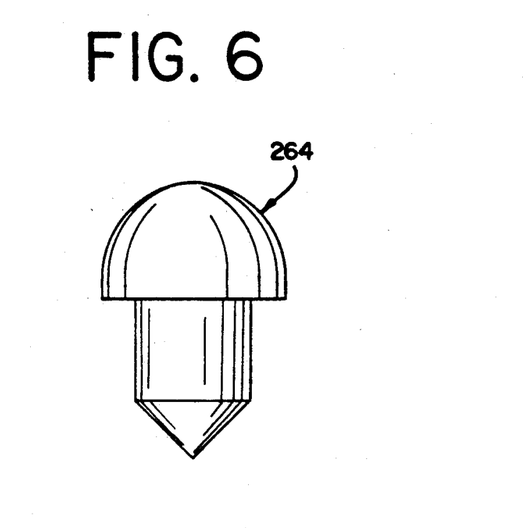
FIG. 6 is a side elevational view of the reflector end plug prior to assembly in the catheter illustrated in FIG. 4.

The second embodiment of the present invention is illustrated in FIGS. 4–6 in the form of a catheter 200 having a optical fiber 220 disposed within a catheter head 236. A reflector member 264 is mounted along a longitudinal axis 260 to a mounting ring 268 that is supported by struts 270. The struts 270 each have a generally circular cross section as illustrated in FIG. 5 rather than the generally triangular cross section of the struts 170 of the first embodiment of the catheter illustrated in FIG. 2. Otherwise, the construction of the catheter 200 is substantially similar to the construction of the first embodiment of the catheter 100. Thus, the laser radiation is substantially laterally reflected as indicated by the arrows 266 in FIG. 4.

If desired, a thermocouple system may be provided for the catheter 200 in substantially the same manner as the thermocouple 188 is provided in the first embodiment of the catheter described above with reference to FIGS. 1–3.

Figure 7:
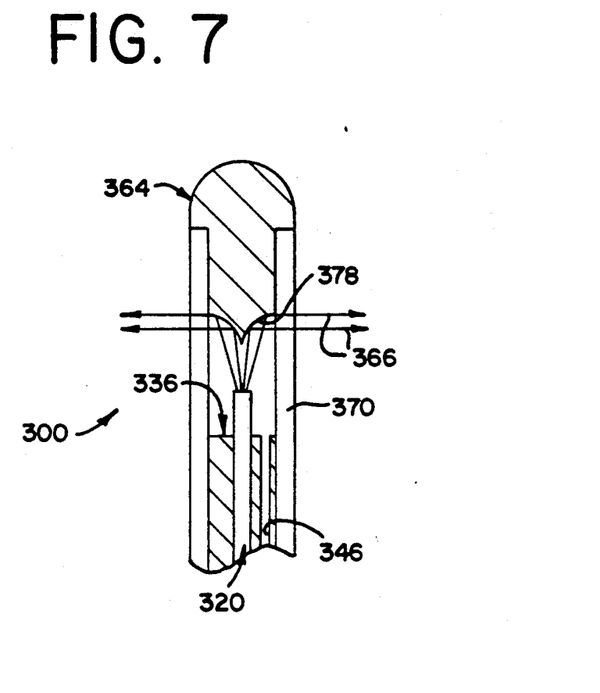
FIG. 7 is a fragmentary, side elevational view, partly in cross section, showing the distal end portion of a third form of a catheter embodying the present invention.

FIG. 7 illustrates a third embodiment of the invention in the form of a catheter designated generally by the reference numeral 300. The catheter 300 includes a head 336 in which is disposed an optical fiber 320. The head 336 also defines a channel or passage 346 for flushing fluid or the like. A reflecting member 364 is mounted to the ends of struts 370 which form a unitary part of the head 336.

The reflecting member 364 is similar to the reflecting member 164 of the catheter 100 described above with reference to FIGS. 1–3 except that the plug 364 has an annular, concave, parabolic reflecting surface 378 rather than a conical reflecting surface. The laser radiation is reflected generally laterally, in a substantially 360° circumferential beam as indicated by the arrows 366, with less divergence than shown in FIG. 1.

A thermocouple system may also be provided in the catheter 300 in a manner similar to that as discussed above with respect to the first and second embodiments of the catheters illustrated in FIGS. 1–6.

Figure 8:
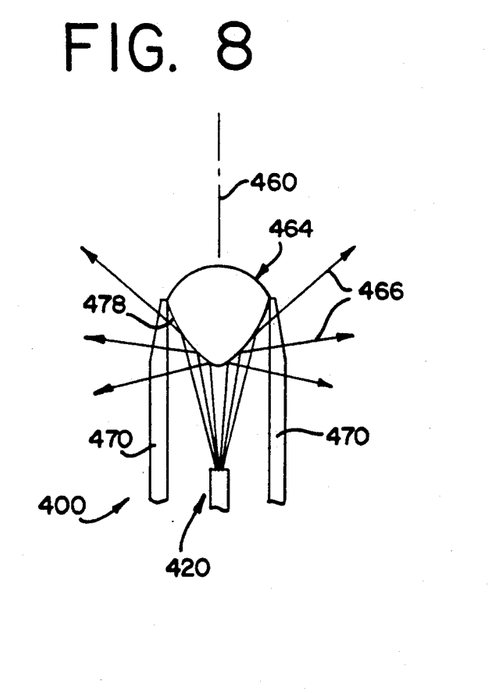
FIG. 8 is a fragmentary, side elevational view, partly in cross section, showing the distal end portion of a fourth form of a catheter embodying the present invention.

FIG. 8 illustrates a fourth embodiment of the invention in the form of a catheter designated generally by the reference numeral 400. The catheter includes a single, solid, optical fiber 420 which is surrounded by three equally spaced-apart struts 470. The struts 470 are unitary with a portion of a catheter head (not illustrated) which can be similar to the head 136 described above with reference to the first embodiment illustrated in FIGS. 1–3.

The struts 470 support a reflector member 464 which may have the same composition as the member 164 of the first embodiment described above with reference to FIGS. 1–3. The reflector member 464 defines a convex reflecting surface 478 which has a substantially paraboloidal shape. The surface 478 functions to defuse the radiation as indicated by the arrows 466. The radiation is nevertheless directed generally laterally to the body site in a 360° circumferential beam. Owing to the defusing effect of the surface 478, the body site can be irradiated for a substantially longer distance along the length of the longitudinal axis 460.

A thermocouple system may be provided in the catheter 400 in a manner analogous to that described above with respect to the first embodiment of the catheter 100 illustrated in FIGS. 1–3.

Figures 9, 10, 11, 12:
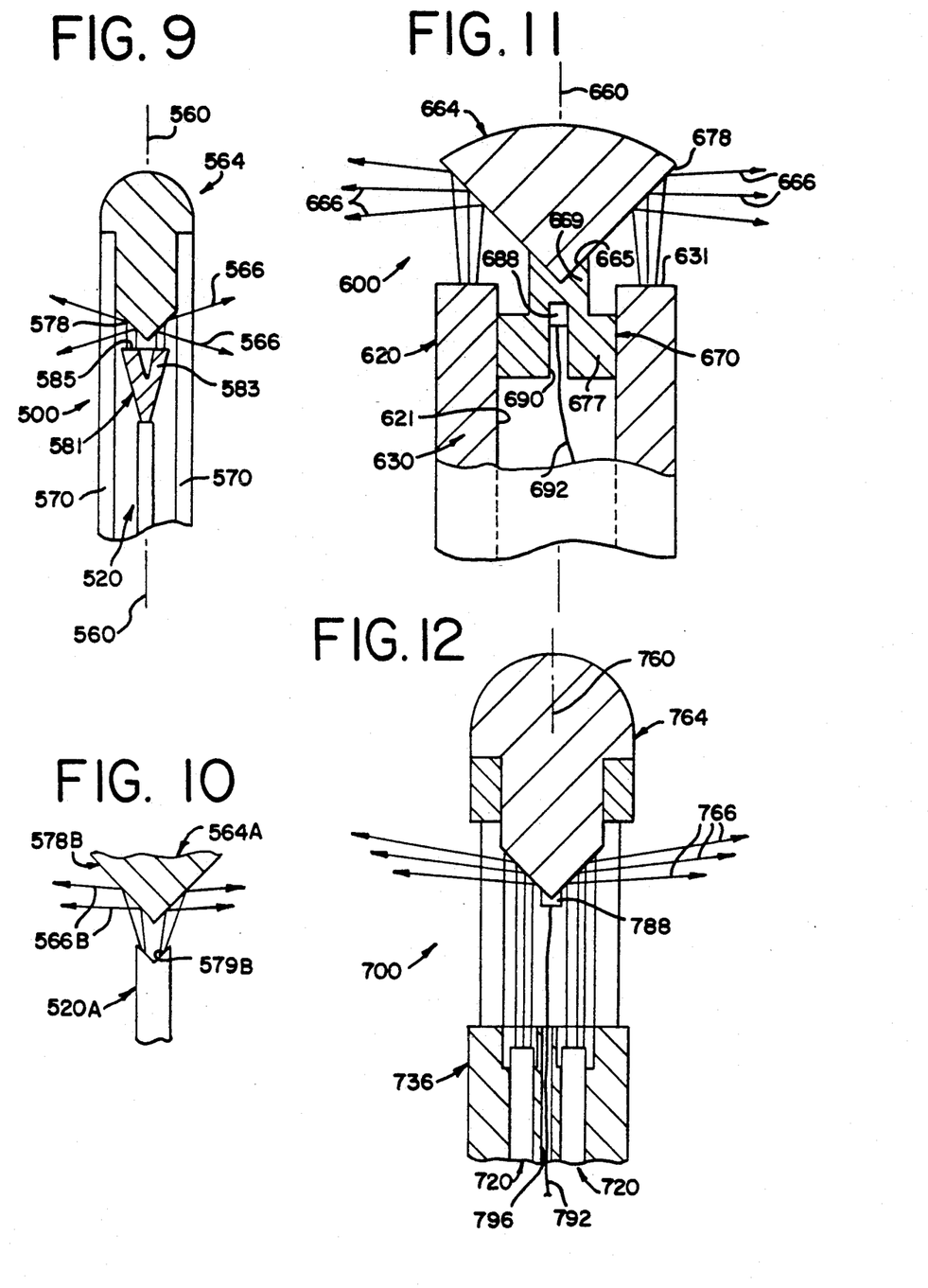
FIG. 9 is a fragmentary, side elevational view, partly in cross section, showing the distal end portion of a fifth form of a catheter embodying the present invention.
FIG. 10 is an enlarged, fragmentary, cross-sectional view similar to FIG. 9 but showing a modification of the catheter illustrated in FIG. 9.
FIG. 11 is a fragmentary, side elevational view, partly in cross section, showing the distal end portion of a sixth form of a catheter embodying the present invention.
FIG. 12 is a fragmentary, side elevational view, partly in cross section, showing the distal end portion of a seventh form of a catheter embodying the present invention.

A fifth embodiment of the present invention in the form of a catheter 500 is illustrated in FIG. 9. The catheter 500 includes an optical fiber 520 centrally disposed within a plurality of struts 570 which are unitary with the lower portion of a catheter head (not illustrated). The lower portion of the head can be similar to the head 136 of the catheter 100 described above with reference to FIGS. 1-3.

The struts 570 support a reflector member 564 which has a conical reflecting surface 578. The structure and operation of the reflector block 564 are substantially identical to the structure and operation of the reflector block 174 described above with reference to the first embodiment illustrated in FIGS. 1-3.

A special beam splitter or diverging device 581 is in contact with, or is at least optically coupled to, the optic fiber 520 so that the radiation transmitted by the fiber 520 is transmitted into the device 581. The device includes a transmitting end portion which has a frustoconical, annular configuration 583 defining an annular end surface 585 for emitting the laser radiation in a generally ring-like, cylindrical beam which is generally parallel to the longitudinal axis 560. The external surfaces may be clad with a material of an appropriate index of refraction (for the laser radiation being used) so as to prevent leakage. The use of the device 581 avoids exposing the tip of the conical reflecting surface 578 to the laser energy, and the surface 578 can still function to reflect the radiation generally laterally of the axis 560 as indicated by the arrows 566. If desired, a thermocouple system can be provided for the catheter 500 in substantially the same manner as described above for the thermocouple system employed in the catheter 100 illustrated in FIGS. 1-3.

FIG. 10 illustrates a modification of the catheter 500 illustrated in FIG. 9. The modified catheter includes an optical fiber 520A and reflector block 564A having a reflecting surface 578B. However, the beam splitter 581 is omitted between the optical fiber 520A and the reflector block 564A. Instead of using the beam splitter to effect divergence of the radiation beam away from the tip of the conical reflecting surface 578B, the distal end of the optical fiber 520A is provided with a generally conical, convex indentation of 579B. The indentation 579B may be formed with a diamond drill. The indentation 579B causes the radiation to be emitted in an outwardly projecting hollow cone, ring, or halo as schematically indicated by the radiation rays 566B. Substantially no radiation is emitted from the center of the cone to impinge on the tip of the reflector block 564A.

A sixth embodiment of the present invention is shown in FIG. 10 in the form of a catheter 600. The catheter 600 employs a single, hollow, elongate, unitary optic fiber 620 rather than a solid fiber as in the previous embodiments.

The fiber 620 has a generally tubular configuration. The transverse cross section is ring-shaped, and, as illustrated in FIG. 10, a central, generally cylindrical channel 621 extends the length of the fiber 620. A hollow optic fiber construction which may be employed in the present invention is disclosed in U.S. Pat. No. 4,768,858.

The hollow fiber 620 has an annular core 630 which may be made of glass or silica quartz. Alternatively, in some applications, the fiber core 630 may be formed from plastic materials such as, for example, methyl methacrylate or polystyrene. In one contemplated embodiment of the present invention, the inner diameter of the core 630 is about 1.5 mm and the outer diameter of the core 630 is about 2.5 mm.

An inner cladding (not illustrated) is disposed to cover the inner cylindrical surface of the fiber core 630, and an outer cladding (not illustrated) is disposed to cover the outer cylindrical surface of the core 630. The same material may advantageously be used for both the inner cladding and the outer cladding.

The cladding material has a refractive index which differs from the refractive index of the fiber core 630. The materials employed for the core inner cladding and outer cladding are selected on the basis of the refractive indexes relative to the core refractive index such that the laser radiation is confined within the fiber core 630 with a minimum attenuation. It is desirable in many applications that the internal reflection caused by the cladding be such that the radiation emitted from the end of the fiber core 630 has a relatively low divergence.

Examples of suitable cladding materials include silicone, silica, plastic or air. Plastic material suitable for cladding includes poly(methylmethacrylate) or a mixture of poly(methylmethacrylate) and polystyrene. In a contemplated embodiment, the cladding is air. If the cladding is a solid, the inner cladding and outer cladding each may have a thickness that is preferably in the range of about 0.06 mm. to about 0.1 mm.

Although not necessary in all applications, a sheath and/or covering (not illustrated) may be disposed around the outer cladding as described above for the first embodiment illustrated in FIGS. 1-3.

The hollow optic fiber 620 may be disposed in a catheter head which supports the fiber 620 adjacent the distal end of the fiber and which may include provisions for fluid flushing (such as channels similar to the channels 146 employed in the first embodiment of the catheter 100 described above with reference to FIGS. 1-3).

The catheter 600 has a distal end region that extends along a longitudinal axis 660. The hollow fiber 620 terminates in a transverse, substantially flat, annular, energy delivery surface 631. The laser radiation transmitted along the fiber core 630 is emitted from the surface 631.

Preferably, a portion of the length of the catheter 600 is flexible. In a contemplated preferred embodiment, the hollow optical fiber has an annular radiation-transmitting core with an inside diameter of about 1.5 mm. and an outside diameter of about 2.5 mm. The fiber is provided in the form of a relatively inflexible, short segment having a length of between about 50 mm. and about 30 mm. as defined between two parallel, flat, annular end faces. The short segment of the annular optical fiber may be indirectly coupled to the laser through a relatively long and flexible, single, conventional, solid core, cylindrical, optical fiber which preferably has a diameter of between about 0.3 mm. and about 1 mm. The solid fiber is coupled at one end to the laser and can be disposed with its other end adjacent an end of the short length of annular optical fiber (as shown in, for example, U.S. Pat. No. 4,465,335 with reference to solid optical fiber 22 and annular optical fiber 14 in FIG. 1). The end of the solid fiber that is adjacent the annular fiber has a flat, circular end face which confronts, and which is approximately parallel to, a portion of the annular face on the proximal end of the annular optical fiber. The laser radiation is emitted from the solid fiber and passes into the proximal end of the annular fiber. The radiation is distributed around the annular fiber and is emitted at the distal end annular face as a generally ring-like beam. Preferably the long, solid optical fiber (and any cladding, optional sheath, and optional covering) are all sufficiently flexible (at least rearwardly of the hollow fiber 620 and any rigid head that may be employed) so as to permit the catheter 600 to be advanced, with or without a surrounding endoscope or other tool, in a lumen or other body cavity.

The exterior surfaces of the catheter 600, which are in contact with the body tissue should preferably be of a material which is biocompatible for the time period during which the catheter will be received within the body cavity.

A reflector means, such as a reflector member or block 664, is positioned axially adjacent the energy delivery surface 631 for intercepting and reflecting the emitted radiation in a beam that radiates substantially transversely of, and substantially around, the axis 660 as schematically indicated by the arrows 666.

The block 664 has a rounded front end surface 674 which is smooth and which is adapted to gently slide past body tissue in the body cavity, such as cavity 12 in FIG. 1, with a minimum of trauma to the tissue. Preferably, at least the rounded front end surface 674 is coated with a non-stick or release coating such as polytetrafluoroethylene to provide easy release from tissue.

The reflector block 664 has a generally conical rear end that includes a conical or frustoconical reflecting surface 678 which is defined around a central axis that is coincident with the longitudinal axis 660. The reflecting surface 678 is oriented to diverge away from the axis 660 with increasing distance from the fiber energy delivery surface 631.

The reflector block 664 may be fabricated from the same materials and provided with the same reflecting coatings as described above for the first embodiment of the reflector plug 164 with reference to FIGS. 1–3.

Further, the angle of the reflecting surface 678 relative to the longitudinal axis 660 is preferably about 45°. Most of the laser radiation (which is preferably emitted from the annular surface 631 in a ring beam generally parallel to the axis 660 (or only slightly divergent therefrom)) will then be reflected substantially transversely of, and substantially around, the axis 660.

In the catheter 600 there are no struts circumferentially spaced around the reflector block 664. Rather, the reflector block 664 is mounted within the central channel 621 of the hollow fiber 620 by means of a mounting member 670. The mounting member 670 has a cylindrical portion 667 secured inside the fiber 620 by suitable means, such as adhesive or the like. The mounting member 670 further includes a reduced diameter, outwardly projecting, cylindrical portion 669 which defines a concave, conical receiving surface 665 for receiving the conical end of the reflector block 664. The block 664 may be secured to the portion 669 by suitable conventional or special means, such as with adhesive.

The catheter 600 provides a completely unobstructed region around the reflector block 664 through which the radiation can be laterally reflected to the body site in a 360° circumferential beam. Further, the use of a hollow fiber 620 for transmitting a ring-like beam to the block 664 serves to keep the laser radiation from impinging at the tip of the conical reflecting surface 678.

Nevertheless, if potential heating of the reflector block 664 is of concern in a particular application, the catheter 600 accommodates the use of a thermocouple and control system similar to that described above for the first embodiment of the catheter 100 illustrated in FIGS. 1–3. In particular, the mounting member 670 may be fabricated from a thermally conductive material and secured to the reflector block 664 in a way that provides a relatively good heat transfer interface between the block 664 and mounting member 670. The mounting member 670 can be provided with a bore 690 for receiving a thermocouple junction 688 which may be suitably secured, as with adhesive, in the bore 690. The thermocouple wire leads 692 may be run from the junction in the bore 690 and through the central channel 621 of the hollow optical fiber 620. The wire leads 692 may be run from the fiber 620 and out of the catheter tubing to a suitable control system (not illustrated) for operation as described above with respect to the first embodiment of the catheter 100.

The catheter 600 can also include appropriate structures defining passages (such as flushing or suction passages 146 for the embodiment illustrated in FIG. 1) if desired, as well as appropriate apertures (not illustrated) in the mounting member 670.

FIG. 12 illustrates a seventh embodiment of the invention in the form of a catheter designated generally by the reference numeral 700. The catheter includes a catheter head 736 to which is mounted a reflector member 764 which is substantially identical to the reflector member 264 described above with reference to the second embodiment illustrated in FIGS. 4–6.

The catheter head 736 accommodates a plurality of circumferentially disposed individual solid optical fibers 720. The radiation transmitted from the ends of the circular array of fibers 720 forms a substantially annular beam which impinges upon the conical reflecting surface of the reflector member 764 so that the radiation is substantially laterally reflected in a 360° circumferential beam as indicated schematically by the arrows 766.

If desired, a thermocouple system may be provided in the catheter 700 to monitor the temperature. The thermocouple junction may be disposed within a housing 788 having a conical recess for being received on the end of the conical reflector member 764 and secured thereto by suitable means. The thermocouple lead wires 792 can be run through a central channel 796 defined within the catheter head 736. In this design, the thermocouple is easily mounted to the exterior of the reflector member 764 on the central axis 760 which does not lie in the optical path of the laser radiation.

It will be appreciated that the present invention provides a novel method for efficiently directing radiation laterally to a body cavity site in a manner that minimizes beam attenuation and trauma to the body tissues.

The apparatus which may be employed to carry out the method does not require a complex design or rotation of the device to provide circumferential, 360° delivery of laser energy to tissue. Nevertheless, the apparatus permits relatively precise control of the radiation beam and can be designed to provide fluid, such as flushing liquid, to the body site.

In accordance with the preceding discussion, further adaptations and variations of the present invention will be readily perceived by a practitioner of the medical instrumentation of arts. Therefore, the present invention should be interpreted in accordance with the language of the following claims and not solely in accordance with the particular embodiments within which the invention has been taught.

What is claimed is:

1. A catheter suitable for coupling to a laser source to direct radiant energy laterally to a selected body cavity site, said catheter comprising:

(a) an elongate, optical fiber adapted for coupling to said laser source and having a distal end region that extends along a longitudinal axis and that terminates in an energy delivery surface for emitting laser radiation transmitted by the fiber;

(b) reflector means exposed to said cavity site and positioned generally axially aligned with said energy delivery surface for reflecting said emitted radiation in a beam radiating substantially transversely of, and substantially around, said axis;

(c) a housing defining a central bore in which said optical fiber is disposed with said fiber energy delivery surface projecting beyond said bore;

said housing including a plurality of struts circumferentially spaced around, and extending beyond, said fiber energy delivery surface;

said housing including a support ring connecting ends of said struts; and said reflector means including a reflector plug mounted to said ring, said plug defining a conical surface that has an apex on said axis and that faces said fiber energy delivery surface.

2. A catheter in accordance with claim 7 in which said reflector means includes a generally conical surface defined around a central axis that is coincident that with said longitudinal axis of said fiber distal end region; and said conical surface is oriented to diverge away from said central axis with increasing distance from said fiber energy delivery surface.

3. The catheter in accordance with claim 7 in which said reflector means has a convex reflector surface generally in the shape of a paraboloid.

4. The catheter in accordance with claim 7 in which said reflector means has a concave reflector surface which has a transverse cross section defining a portion of a parabolic curve.

5. The catheter in accordance with claim 1 in which said housing includes three of said struts.

6. The catheter in accordance with claim 1 further including beam splitting means adjacent said fiber energy delivery surface for receiving said radiation from said fiber energy delivery surface and transmitting said radiation in an annular beam to said reflector means.

7. The catheter in accordance with claim 1 including a housing supporting said optical fiber and said reflector means, and defining passages for supplying fluid to said body cavity site.

8. A catheter in accordance with claim 1 in which
said reflector means includes a reflecting member having a rounded front surface and a conical rear surface defined around a central axis that is coincident with said longitudinal axis of said fiber distal end region; and said conical rear surface is oriented to diverge away from said central axis with increasing distance from said fiber energy delivery surface.

9. The catheter in accordance with claim 1 in which said reflector means includes a metallic coating defining a reflecting surface.

* * * * *

UNITED STATES PATENT AND TRADEMARK OFFICE
CERTIFICATE OF CORRECTION

PATENT NO. : 5,242,438

DATED : September 7, 1993

INVENTOR(S) : Vahid Saadatmanesh et al.

It is certified that error appears in the above-identified patent and that said Letters Patent is hereby corrected as shown below:

Col. 1, line 39, "360 arc." should be -- 360° arc. --;

Col. 10, line 9, after "catheter" insert -- 100 --;

Col. 15, line 23, "claim 7" should be -- claim 1 --;

Col. 16, line 1, "claim 7" should be -- claim 1 --;

Col. 16, line 4, "claim 7" should be -- claim 1 --;

Col. 16, lines 15-17, delete "including a housing supporting said optical fiber and said reflector means,".

Signed and Sealed this

Fifteenth Day of March, 1994

Attest:

BRUCE LEHMAN

Attesting Officer

Commissioner of Patents and Trademarks